(12) United States Patent
Lin et al.

(10) Patent No.: US 11,078,144 B2
(45) Date of Patent: Aug. 3, 2021

(54) PROCESS FOR SYNTHESIZING OF HYDROQUINONE DERIVATIVES WITH HEPTADECATRIENYL SIDE CHAIN

(71) Applicant: Institute of Nuclear Energy Research, Atomic Energy Council, Executive Yuan, R.O.C, Taoyuan (TW)

(72) Inventors: Kun-Liang Lin, Taoyuan (TW); Ping-Yen Wang, Taoyuan (TW); Mei-Hui Wang, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 0 days.

(21) Appl. No.: 16/662,308

(22) Filed: Oct. 24, 2019

(65) Prior Publication Data
US 2021/0122690 A1 Apr. 29, 2021

(51) Int. Cl.
| | | |
|---|---|---|
| *C07C 37/055* | (2006.01) |
| *C07C 67/40* | (2006.01) |
| *C07C 67/293* | (2006.01) |
| *C07C 67/29* | (2006.01) |
| *C07C 37/50* | (2006.01) |
| *C07C 67/287* | (2006.01) |
| *C07C 41/30* | (2006.01) |

(52) U.S. Cl.
CPC .......... *C07C 37/0555* (2013.01); *C07C 37/50* (2013.01); *C07C 41/30* (2013.01); *C07C 67/287* (2013.01); *C07C 67/29* (2013.01); *C07C 67/293* (2013.01); *C07C 67/40* (2013.01)

(58) Field of Classification Search
CPC ... C07C 37/0555; C07C 67/293; C07C 67/40; C07C 67/29; C07C 67/287; C07C 41/30; C07C 37/50
See application file for complete search history.

(56) References Cited

U.S. PATENT DOCUMENTS

2004/0110847 A1* 6/2004 Wu ........................ C07C 37/004
514/734

FOREIGN PATENT DOCUMENTS

WO 0190717 A2 11/2001

OTHER PUBLICATIONS

Miyokoshi et al, Bulletin of the Japanese Chemical Society, Synthesis of Urushiols with Pentadecatrienyl Side Chain, Two Constituents of the Sap of a Lac Tree, *Rhus vernicifera*, 1991, 64, pp. 2560-2562. (Year: 1991).*

Maggi et al, Tetrahedron Letters, Rate enhancing and rate retarding effects of methoxy substituents on arene metalation, 1999, 40, pp. 8797-8800. (Year: 1999).*

(Continued)

*Primary Examiner* — Deborah D Carr
(74) *Attorney, Agent, or Firm* — Locke Lord LLP; Tim Tingkang Xia, Esq.

(57) ABSTRACT

Disclosed herein is a process for chemically synthesizing of hydroquinone derivatives, especially for hydroquinone derivatives with heptadecatrienyl side chain, which is synthesized via a Wittig reaction of 2-(10'-oxononyl)-1,4-diacetoxyl benzene and (3E, 5Z)-3,5-heptadien-1-triphenylphosphonium iodide and then deacetylation. In addition, the product is solid powder.

3 Claims, 3 Drawing Sheets

(56) References Cited

OTHER PUBLICATIONS

Tidwell, Organic Reactions, Organic Reactions, Oxidation of Alcohols to Carbonyl Compounds via Alkoxysulfonium Ylides: The Moffatt, Swern, and Related Oxidations, 2004, pp. 1-150. (Year: 2004).*
Greene, Protective Groups in Organic Chemistry, 1981, John Wiley & Sons, New York, pp. 101-102. (Year: 1981).*
Bora, Asian Journal of Chemistry, An Eco-friendly and Mild Process for Deacetylation Reactions in Water, 2011,23(2) pp. 941-942. (Year: 2011).*
Miyakoshi et al., Synthesis of Urushiols with Pentadecatrienyl Side Chain, Two Constituents of the Sap of a Lac Tree, *Rhus vernicifera*, The Chemical Society of Japan, 1991, 64, 2560-2562.
Qi et al., Novel C15 Triene Triazole, D-A Derivatives Anti-HepG2, and as HDAC2 Inhibitors: A Synergy Study, International Journal of Molecular Sciences, 2018, 19, 3184.
Huang et al., Anticancer activity of botanical alkyl hydroquinones attributed to topoisomerase II poisoning, Toxicology and Applied Pharmacology, 2008, 227, 331-338.

\* cited by examiner

PROCESS FOR SYNTHESIZING OF HYDROQUINONE DERIVATIVES WITH HEPTADECATRIENYL SIDE CHAIN

BACKGROUND

Technical Field

This application relates to a process for chemically synthesizing of hydroquinone derivatives, especially for hydroquinone derivatives with heptadecatrienyl side chain.

Related Art

An anticancer drug mainly composed of a catechol derivative can inhibit a type II histone deacetylase according to studies, and thus has therapeutic potential for tumors capable of expressing the type II histone deacetylase, and can be used as an anticancer drug for some tumors. However, the current synthesis methods are based on catechol, but catechol is easily oxidized by light and water at room temperature, and has poor long-term stability and is an oily mixture.

In 1991, Miyakoshi et al. proposed a method for synthesizing of triolefin urushiol having a main structure of C15 carbon chain 3-substituted catechol (Bull. Chem. Soc. Jpn., 64, 2560-2562, 1991.), but a precursor of the method, catechol, is an ortho-dihydroxybenzene compound which is not a stabilizing substance. It is synthesized from 1,2-dimethoxybenzene as a starting material to obtain pentadecatriene alkyl catechol. This compound is a derivative of urushiol used for lacquering. If the pentadecatriene alkyl catechol is further modified with a side chain triazolylamine, it can inhibit the type II histone deacetylase, and has therapeutic potential for tumors capable of expressing the type II histone deacetylase, but is different from heptadecatrienyl hydroquinone in this application. The pentadecatriene alkyl catechol can be made into a final product by deacetylation by the method described in the previous journal, but this method does not apply to the final step of this application, and a factice-like product can be obtained by the above-mentioned deacetylation method, and a solid product can be obtained after this application is improved.

In addition, an anticancer drug mainly composed of hydroquinone derivatives can inhibit topoisomerase 2 according to studies, and topoisomerase 2 is required for proliferation of all tumor cells, but this compound is mainly extracted by Rhus succedanea. However, because of the difficulty in obtaining raw materials and limited resources, the yield is limited.

In view of this, it is necessary to provide a novel chemical synthesis method in the technical field to reduce the deficiencies of the related art.

SUMMARY

To provide a reader with a basic understanding of the present disclosure, the summary provides a brief description of the disclosure. The summary is not a complete description of the disclosure, and is not intended to limit the technical features or the scope of this application.

To resolve the shortcomings of the related art, this application provides a novel preparation method, including using hydroquinone as a starting material to synthesize oxynonyl-acetoxyl benzene, subjecting oxynonyl-acetoxyl benzene to a Wittig reaction with heptadien-triphenylphosphine to obtain heptadecatrienyl alkyl acetoxybenzene, and obtaining the final solid pure heptadecatrienyl hydroquinone by sodium methoxide in methanol. The advantage of this application is that hydroquinone as the starting material is more stable than catechol and a product is non-oily but solid pure substance. Secondly, the deacetylation protection method in the related art (the anticancer drug mainly composed of catechol derivatives) is to deacetylate by LiAlH4, but the method of this application cannot obtain the final product heptadecatrienyl hydroquinone by the former method, but can obtain a high-purity solid product by deacetylation with sodium methoxide, and does not produce other oxidation of acyl bonds, and is better than LiAlH4 deacetylation method in the related art.

A sample of this application is to provide a method of preparing hydroquinone derivatives with heptadecatrienyl side chain, including:

(a) subjecting dimethoxybenzene to bromoalkylation and demethylation reactions to generate a compound of formula (3)

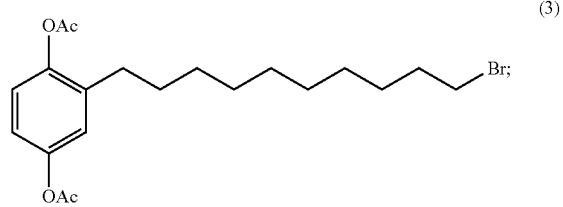 [SMILES: CC(=O)Oc1ccc(OC(C)=O)c(CCCCCCCCCCBr)c1]

(b) subjecting the compound of formula (3) to iodination and oxidization reactions to generate a compound of formula (5)

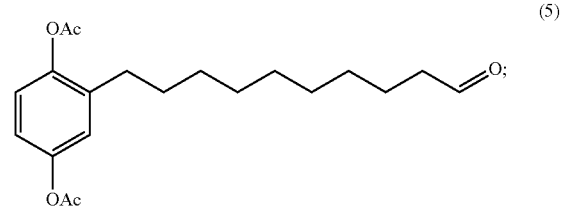 [SMILES: CC(=O)Oc1ccc(OC(C)=O)c(CCCCCCCCCC=O)c1]

and (c) subjecting the compound of formula (5) and heptadien-1-triphenylphosphonium iodide to a Wittig reaction and a deacetylation reaction to obtain hydroquinone derivatives with heptadecatrienyl side chain; for example, a compound of formula (12)

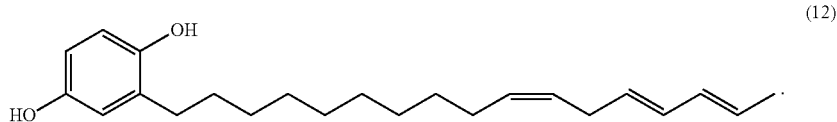 [SMILES: C/C=C/C=C/C/C=C\CCCCCCCCCc1cc(O)ccc1O]

According to a specific implementation method of this application, the heptadien-1-triphenylphosphonium iodide in step (c) includes a compound of formula (10)

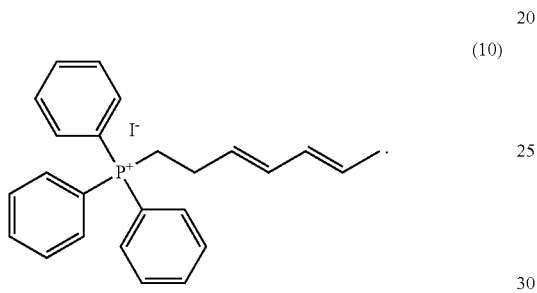

According to another implementation method of this application, in step (c), the hydroquinone derivative with heptadecatrienyl side chain is a compound of formula (11)

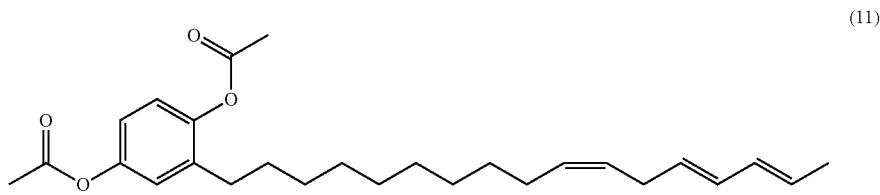 [SMILES: C/C=C/C=C/C/C=C\CCCCCCCCCc1cc(OC(C)=O)ccc1OC(C)=O]

obtained by subjecting the compound of formula (5) and the compound of formula (10) to the Wittig reaction.

According to other implementation methods of this application, the deacetylation reaction in step (c) is carried out by subjecting the compound of formula (11) to the deacetylation reaction to obtain a compound of formula (12)

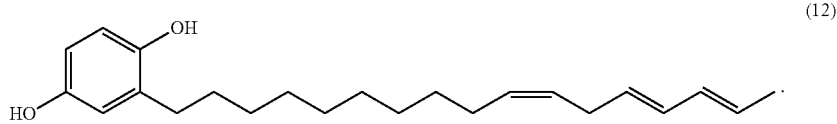 [SMILES: C/C=C/C=C/C/C=C\CCCCCCCCCc1cc(O)ccc1O]

In addition, in an implementation method of this application, the deacetylation reaction in step (c) is carried out by reacting the compound of formula (11) with sodium methoxide in methanol at room temperature.

In an implementation method of this application, the bromoalkylation reaction of dimethoxybenzene in step (a) is carried out by activating dimethoxybenzene with n-butyl lithium and then reacting with 1,10-dibromodecane by one step to obtain a compound of formula (1)

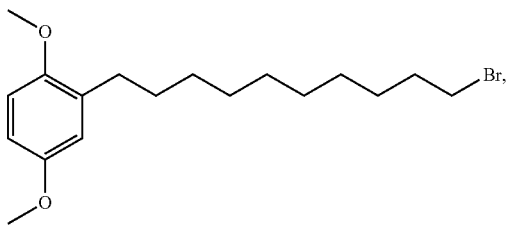

(1)

then reacting with boron tribromide to demethylate to obtain a compound of formula (2)

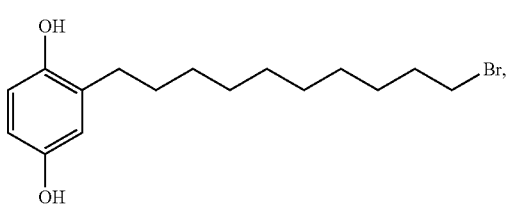

(2)

and finally, reacting acetic anhydride with pyridine to obtain the compound of formula (3).

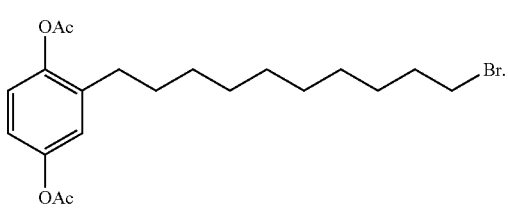

(3)

According to an implementation method of this application, the iodination reaction in step (b) is carried out by adding sodium iodide to react to obtain a compound of formula (4)

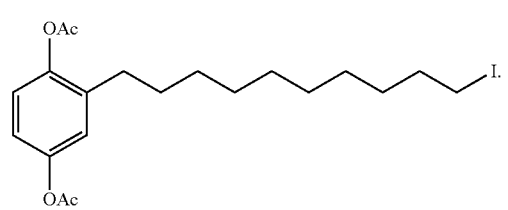

(4)

According to the specific implementation methods of this application, the oxidation reaction in step (b) is carried out by mixing the compound of formula (4) with dimethyl sulfoxide and benzene, and then adding sodium hydrogen carbonate to subject to a heating reflux reaction to obtain the compound of formula (5).

The central concept, the technical means employed, and various samples of this application can be fully understood by those of ordinary skill in the art after referring to the following implementation methods.

BRIEF DESCRIPTION OF THE DRAWINGS

To make the above and other objects, features, advantages and embodiments of this application more apparent and understood, the drawings are described as follows.

DETAILED DESCRIPTION

To make the description of the present disclosure more detailed and complete, the following illustrative written description of the samples and embodiments of this application are set forth below, but the samples and embodiments of this application are not limited thereto.

Unless otherwise indicated, the scientific and technical proper nouns used herein have the same meaning as commonly understood by those of ordinary skill in the art. Furthermore, the nouns used herein are intended to cover the singular and plural types of the nouns unless otherwise specified.

As used herein, the term "about" generally means that the actual value is within plus or minus 10%, 5%, 1%, or 0.5% of a particular value or range. The term "about" is used herein to mean that the actual value falls within an acceptable standard error scope of the mean, as determined by those of ordinary skill in the art. It should be understood that the scopes, quantities, numerical values, and percentages used herein are modified by the term "about" with the exception of experimental examples, or unless otherwise specified. Therefore, unless otherwise indicated, the numerical values or parameters disclosed in the specification and the appended claims are all approximate values and can be changed according to demand.

This application is characterized by providing a chemical synthesis method of hydroquinone derivatives with heptadecatrienyl side chain, including: using a stable methylation-protected hydroquinone (1,4-dimethoxybenzene) as a starting material, subjecting 1,4-dimethoxybenzene to bromoalkylation, demethylation protection and acetylation protection, iodination, and side oxylation to form 2-(10'-oxononyl)-1,4-diacetoxyl benzene; and then subjecting 2-(10'-oxononyl)-1,4-diacetoxyl benzene to the Wittig reaction with (3E, 5Z)-3,5-heptadien-1-triphenylphosphonium iodide and then deacetylation to form heptadecatrienyl hydroquinone.

The technical content shown in an implementation method of this application relates to a method for preparing a compound of formula (12)

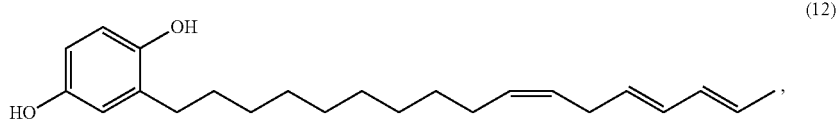 [SMILES: C/C=C/C=C/C/C=C\CCCCCCCCCc1cc(O)ccc1O]

Figure 1:
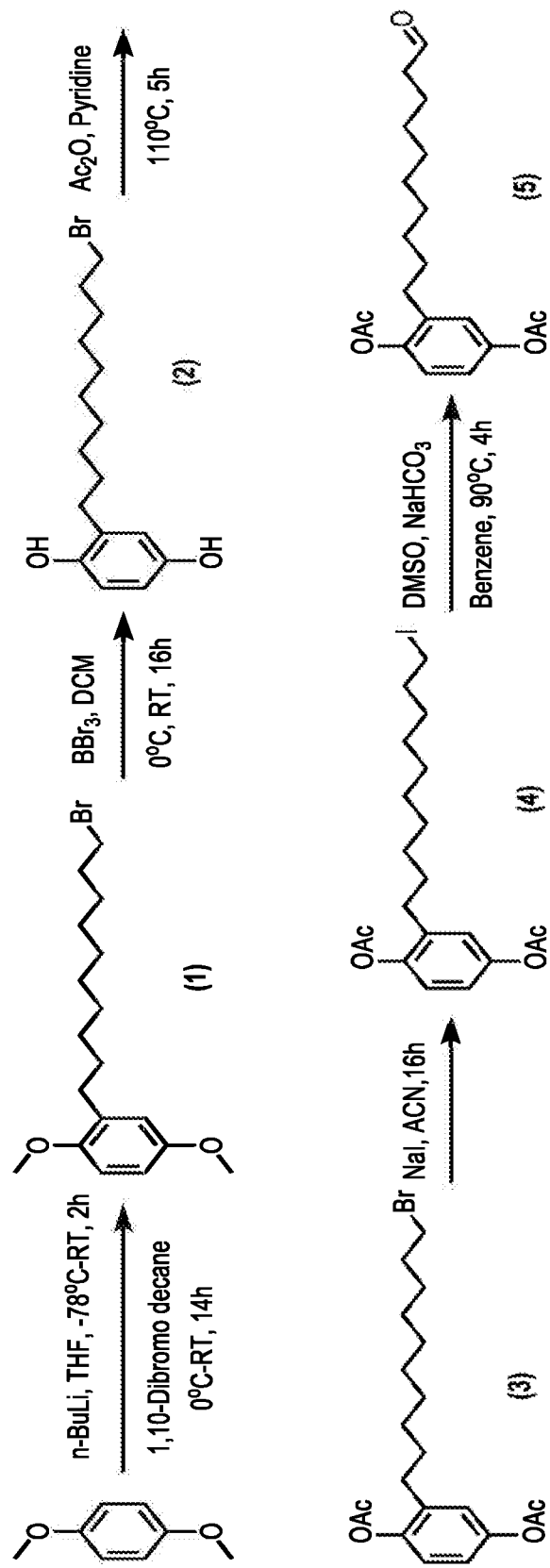
FIG. 1 is a flow chart showing the synthesis of a compound of formula (5) according to an implementation method of this application.
Figure 2:
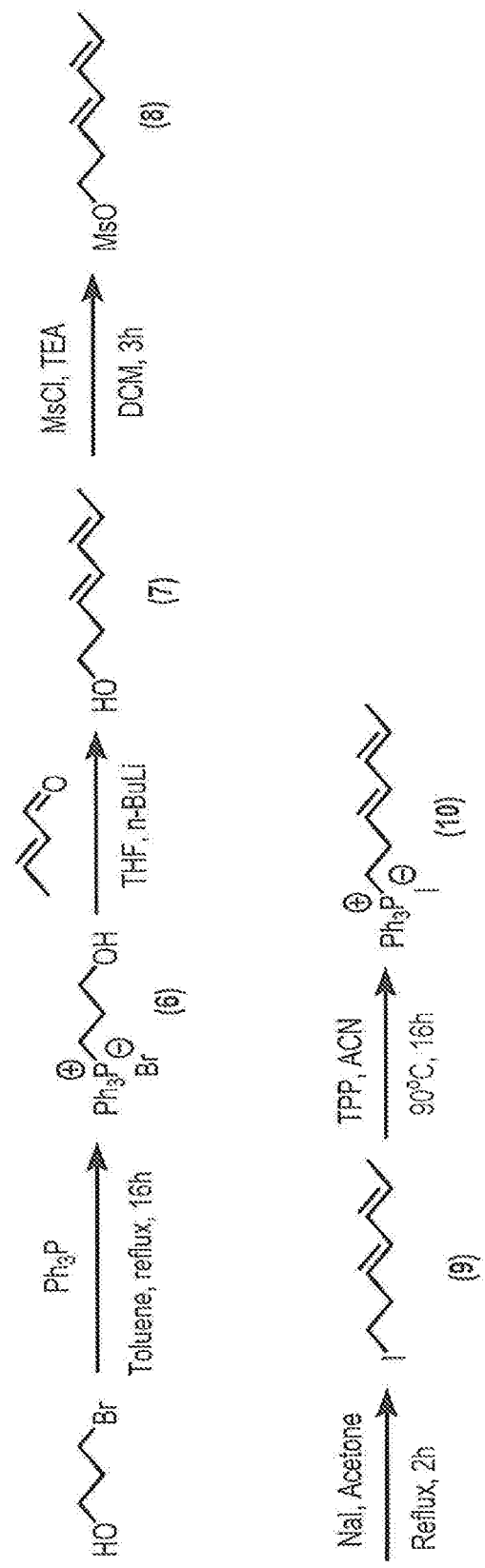
FIG. 2 is a flow chart showing the synthesis of a compound of formula (10) according to an implementation method of this application.
Figure 3:
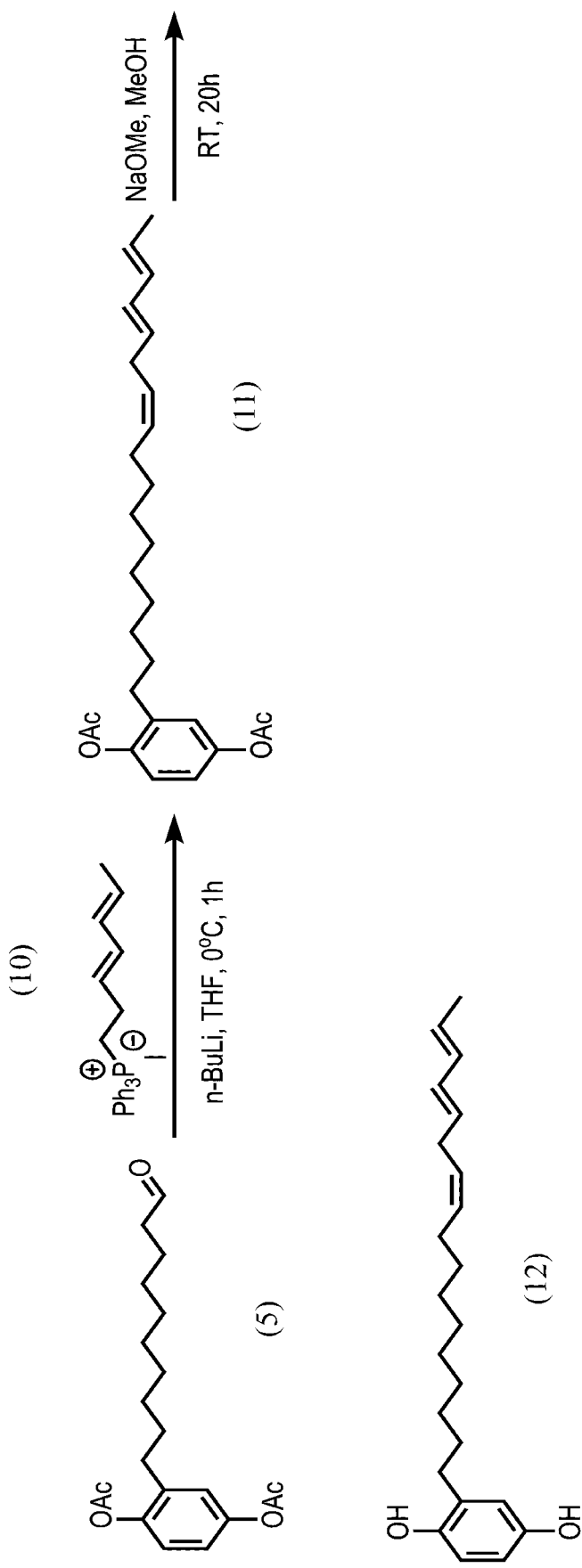
FIG. 3 is a flow chart showing the synthesis of a compound of formula (12) according to an implementation method of the present invention.

(12)

and the detailed steps refer to FIG. 1 to FIG. 3.

To synthesize the compound of formula 12, firstly, an intermediate product needs to be synthesized. Please referring to FIG. 1, 1,4-methoxy benzene was mixed with 1,10-dibromodecane to be alkylated, and demethylated with boron tribromide in an ice bath, and then heated to reflux with acetic anhydride to be acetylated to obtain a compound of formula (3). Next, an iodination reaction was carried out, and then an oxidation reaction was carried out with DMSO-NaHCO$_3$ in a benzene solution to obtain a compound of formula (5).

Please referring to FIG. 2, 3-bromopropanol as a starting material was firstly reacted with triphenylphosphine to form a dipole body, and then reacted with the dipole body and butadiene aldehyde to generate heptadienol through the Wittig reaction, then heptadienol and methane sulfonyl chloride are subjected to a substitution reaction, and further subjected to an iodination reaction, and finally subjected to a dipolarization reaction with triphenylphosphine to obtain a compound of formula (10).

Please referring to FIG. 3, the compound of formula (5) and the compound of formula (10) (3, 5-heptadien-1-triphenylphosphonium iodide, see FIG. 2 for the synthesis method) were subjected to the Wittig reaction to obtain a compound of formula (11). The compound was further reacted with sodium methoxide in methanol and stirred at room temperature overnight to obtain the compound of formula (12).

Embodiment 1 Method for Preparing Heptadecatrienyl Hydroquinone Compound of Formula (12)

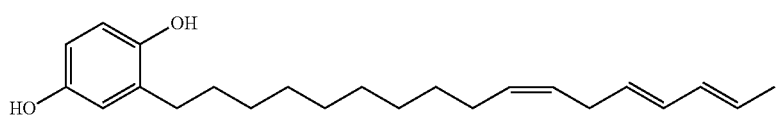

Embodiment 1.1 Preparation of Compound of Formula (1)

1,4-dimethoxybenzene (10 g, 72.4 mmol) and n-butyllithium (5.8 g, 90.5 mmol) were taken and put in a round-bottom flask, and added with a tetrahydrofuran solvent (200 mL), and then the reaction flask was placed in a low temperature reactor; after stirring was carried out at a temperature of −78° C. for 1 hour, the reaction flask was transferred to room temperature and stirring was carried out for 1 hour; a single-neck flask was additionally prepared, 1,10-dibromodecane (65.17 g, 217.2 mmol) was taken and dissolved in tetrahydrofuran (100 mL), and the solution was slowly dropped into the original solution, and then stirred at room temperature for 14 hours, and then the product was purified by a silica gel column to obtain 17 g of a product, which is 2-(10'-bromodecyl)-1,4-dimethoxybenzene (namely, a compound of formula (1)), with a yield of 65%.

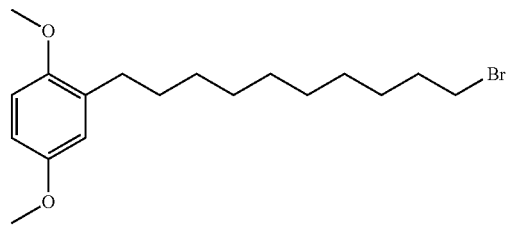

(1)

$^1$H NMR (500 MHz, CDCl$_3$) δ 6.75-6.76 (d, J=4 Hz, 1H, 6-H), 6.72 (d, J=2.5 Hz, 1H, 3-H), 6.67 (dd, J=9, 2.5 Hz, 1H, 5-H), 3.77 (s, 6H, 1-OCH$_3$ and 4-OCH$_3$), 3.40 (t, J=6.5 Hz, 2H, 10'-CH$_2$), 2.56 (t, J=7.5 Hz, 2H, 1'-CH$_2$), 1.84 (m, 2H, 9'-CH$_2$), 1.53-1.58 (m, 2H, 2'-CH$_2$), 1.38-1.43 (m, 2H, 8'-CH$_2$), 1.28-1.37 (m, 10H, 3' to 7'-(CH$_2$)$_5$).

Embodiment 1.2 Preparation of Compound of Formula (2)

The compound of formula (1) (5 g, 14.0 mmol) was taken from a round-bottom flask and dissolved in dichloromethane (300 mL), slowly added drop wise with boron tribromide (4 mL, 42 mmol) in an ice bath, and stirred at room temperature for 16 hours, and then the product was purified by a silica gel column to obtain 3.5 g of a product, which is 2-(10'-bromodecyl)-1,4-dihydrooxybenzene (a compound of formula (2)), with a yield of 76%.

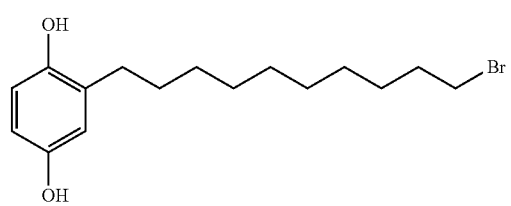

(2)

$^1$H NMR (500 MHz, CDCl$_3$) δ 6.3-6.65 (d, J=8.5 Hz, 1H, 6-H), 6.62 (d, J=2.5 Hz, 1H, 3-H), 6.53-6.56 (dd, J=8.5, 2.5 Hz, 1H, 5-H), 3.40 (t, J=6.5 Hz, 2H, 10'-CH$_2$), 2.54 (t, J=7.5 Hz, 2H, 1'-CH$_2$), 1.85 (m, 2H, 9'-CH$_2$), 1.56-1.60 (m, 2H, 2'-CH$_2$), 1.38-1.43 (m, 2H, 8'-CH$_2$) 1.25-1.33 (m, 10H, 3' to 7'-(CH$_2$)$_5$).

Embodiment 1.3 Preparation of Compound of Formula (3)

The compound 2 of formula (2) (16 g, 48.6 mmol) was taken from a round-bottom flask and dissolved in pyridine (100 mL), added with acetic anhydride (7.1 mL, 97.2 mmol) at room temperature, stirred under reflux at a temperature of 110° C. for 5 hours, and then concentrated under reduced pressure, and the product was purified by silica gel chromatography to obtain 13 g of a product, which is 2-(10'-bromodecyl)-1,4-diacetoxyl benzene (namely, a compound of formula (3)), with a yield of 64%.

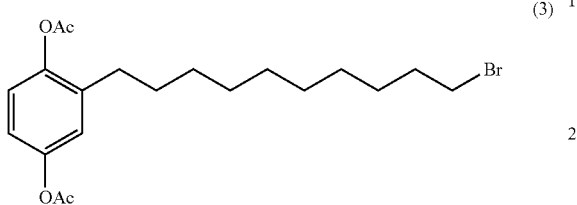

(3)

$^1$H NMR (500 MHz, CDCl$_3$) δ 7.00-7.02 (d, J=8.5 Hz, 1H, 6-H), 6.96 (d, J=2.5 Hz, 1H, 3-H), 6.91-6.94 (dd, J=8.5, 2.5 Hz, 1H, 5-H), 3.40 (t, J=6.5 Hz, 2H, 10'-CH$_2$), 2.48 (t, J=7.5 Hz, 2H, 1'-CH$_2$), 2.30 (s, 3H, 1-COCH$_3$), 2.28 (s, 3H, 4-COCH$_3$), 1.85 (m, 2H, 9'-CH$_2$), 1.52-1.55 (m, 2H, 2'-CH$_2$), 1.39-1.43 (m, 2H, 8'-CH$_2$) 1.28-1.37 (m, 10H, 3' to 7'-(CH$_2$)$_5$).

Embodiment 1.4 Preparation of Compound of Formula (4)

The compound of formula (3) (5.0 g, 12.1 mmol) was taken from a round-bottom flask and dissolved in acetonitrile, added with sodium iodide (2.7 g, 18.2 mmol), and then stirred for 16 hours; after the reaction was finished, the product was purified by a silica gel column to obtain 2-(10'-iododecyl)-1,4-diacetoxyl benzene (4 g) (a compound of formula (4)), with a yield of 71%.

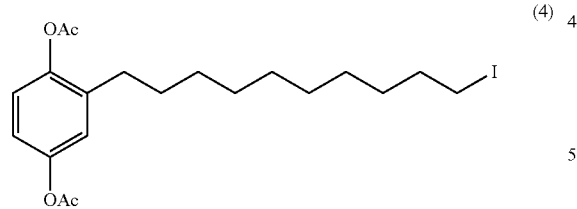

(4)

$^1$H NMR (500 MHz, CDCl$_3$) δ 7.00-7.02 (d, J=8 Hz, 1H, 6-H), 6.96 (d, J=3 Hz, 1H, 3-H), 6.91-6.94 (dd, J=8.5, 2 Hz, 1H, 5-H), 3.18 (t, J=6.5 Hz, 2H, 10'-CH$_2$), 2.48 (t, J=7.5 Hz, 2H, 1'-CH$_2$), 2.30 (s, 3H, 1-COCH$_3$), 2.28 (s, 3H, 4-COCH$_3$), 1.81 (m, 2H, 9'-CH$_2$), 1.52-1.57 (m, 2H, 2'-CH$_2$), 1.35-1.39 (m, 2H, 8'-CH$_2$) 1.28-1.34 (m, 10H, 3' to 7'-(CH$_2$)$_5$).

Embodiment 1.5 Preparation of Compound of Formula (5)

The compound of formula (4) (2 g, 4.3 mmol) was taken and put in a round-bottom flask with dimethyl sulfoxide (100 mL) and benzene (100 mL) as solvents, then added with sodium bicarbonate and stirred under reflux at a temperature of 90° C. for 4 hours, and then added with water (100 mL), an organic layer was taken and quenched and washed twice with a 0.1 N hydrochloric acid solution, and then quenched and washed once with a saturated salt solution, the organic layer was taken and concentrated under pressure after water was removed by sodium sulfate, and the product was separated and purified by a silica gel column to obtain 2-(10'-oxononyl)-1,4-diacetoxyl benzene (1.4 g) (a compound of formula (5)), with a yield of 96%.

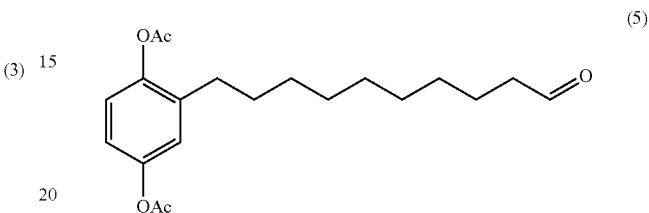

(5)

$^1$H NMR (500 MHz, CDCl$_3$) δ 9.76 (s, 1H, 10'-H), 7.00-7.02 (d, J=8 Hz, 1H, 6-H), 6.96 (d, J=3 Hz, 1H, 3-H), 6.91-6.94 (dd, J=8.5, 2 Hz, 1H, 5-H), 2.48 (t, J=7.5 Hz, 2H, 9'-CH$_2$), 2.41 (t, J=7.5 Hz, 2H, 1'-CH$_2$), 2.31 (s, 3H, 1-COCH$_3$), 2.28 (s, 3H, 4-COCH$_3$), 1.60 (m, 2H, 8'-CH$_2$), 1.51-1.56 (m, 2H, 2'-CH$_2$), 1.24-1.36 (m, 10H, 3' to 7'-(CH$_2$)$_5$).

Embodiment 1.6 Preparation of Compound of Formula (6)

3-bromopropanol (55.6 g, 0.4 mol) and triphenylphosphine (150 g, 0.6 mol) were taken and put in a round-bottom flask, and added with toluene (200 mL) to be dissolved, and the solution was stirred under reflex at a temperature of 110° C. for 16 hours; after cooled to room temperature, the solution was added with ethyl ether so that the product was precipitated to obtain (3-hydroxypropyl)triphenylphosphonium bromide (160 g) (a compound of formula (6)), with a yield of 99%.

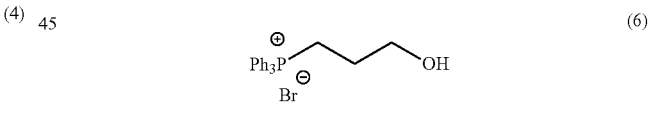

(6)

$^1$H NMR (500 MHz, DMSO-D$_6$) δ 7.59-7.92 (m, 15H, -(phenyl)$_3$), 3.52-3.61 (m, 4H, 2, 3-CH$_2$CH$_2$), 1.63-1.70 (m, 2H, 1-CH$_2$).

Embodiment 1.7 Preparation of Compound of Formula (7)

The compound of formula (6) (103 g, 0.26 mol) was taken and dissolved in anhydrous tetrahydrofuran (100 mL), added with n-butyl lithium (208 mL, 2.5 M in hexane, 0.52 mol) in a 0° C. ice bath, and continuously stirred for half an hour in a 0° C. ice bath, then added with bis-crotonaldehyde (25.8 mL, 0.31 mol) and continuously stirred for 1 hour, and then added with saturated ammonium chloride (100 mL) to terminate the reaction, the product was extracted twice with ethyl ether (50 mL×2), organic layers were combined, pressure reduction, concentration and draining were performed, and the product was purified by silica gel column chromatography to obtain (3E, 5E)-3, 5-heptadien-1-ol (18.6 g) (a compound of formula (7)), with a yield of 62%.

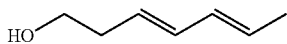
(7)

¹H NMR (500 MHz, CDCl₃) δ=1.55-1.78 (d, 3H, 7-CH₃), 2.31-2.47 (dt, 2H, 2-CH₂), 3.67 (m, 2H, 1-CH₂OH), 5.48-5.54 (dt, 1H, 6-=CH—CH₃), 5.63-5.76 (dq, 1H, 3-CH=CH), 6.01-6.34 (m, 2H, 4-=CH—CH and 5-CH=CH).

Embodiment 1.8 Preparation of Compound of Formula (8)

The compound of formula (7) (0.5 g, 4.46 mmol) was taken and dissolved in dichloromethane (100 mL), then added with methane sulfonyl chloride (414.1 mL, 5.35 mmol) and triethylamine (932.4 mL, 6.69 mmol) in a 0° C. ice bath, transferred to room temperature and stirred for 3 hours, and added with dichloromethane (100 mL) to dilute the solution, and the solution was quenched and washed twice with 1 M hydrochloric acid (50 mL), and quenched and washed twice with saturated sodium carbonate (50 mL), and finally quenched and washed once with saturated salt (50 mL), then organic layers were combined, and then concentrated under reduced pressure after water was removed with sodium sulfate, without purifying any more in this step, to obtain (3E, 5E)-3, 5-heptadien-1-methylsulfonic acid (630 mg) (a compound of formula (8)), with a yield of 74%.

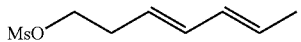
(8)

Embodiment 1.9 Preparation of Compound of Formula (9)

In a round-bottom flask, the compound of formula (8) (620 mg, 3.26 mmol) was taken and dissolved in acetone (50 mL), and added with sodium iodide (1.46 g, 9.78 mmol) and copper powder (6.9 mg, 0.1 mmol) in a 0° C. ice bath to react under reflux at a temperature of 60° C. for 2 hours; after the reaction was finished, the solution was added with saturated sodium thiosulfate (50 mL) and extracted with dichloromethane (50 mL), and an organic layer was taken and concentrated. The product was purified by a silica gel chromatography column to obtain (2E, 4E)-7-iodo-2, 4-heptadiene (600 mg) (compound of formula (9)), with a yield of 82%.

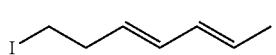
(9)

¹H NMR (500 MHz, CDCl₃) δ=1.72-1.78 (d, 3H, 1-CH₃), 2.60-2.77 (dt, 2H, 6-CH₂), 3.15 (m, 2H, 7-CH₂), 5.43-5.49 (dt, 1H, 2-CH=CH), 5.63-5.78 (dq, 1H, 5-=CH—CH₂), 6.00-6.09 (m, 2H, 3-=CH—CH and 4-CH=CH).

Embodiment 1.10 Preparation of Compound of Formula (10)

The compound of formula (9) (2.2 g, 9.9 mmol) was taken and dissolved in acetonitrile (200 mL), and added with triphenylphosphine (3.9 g, 14.8 mmol) and stirred under reflux at a temperature of 90° C. for 16 hours. The solution was filtered after the stirring was finished, then the solution was concentrated under reduced pressure, and an oily product was washed with ethyl ether and dried to obtain 2.5 g of an oily product, which is (3E, 5E)-3, 5-heptadien-1-triphenylphosphonium iodide (a compound of formula (10)), with a yield of 70%.

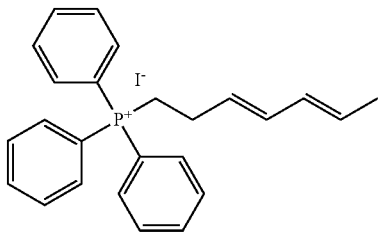
(10)

Embodiment 1.11 Preparation of Compound of Formula (11)

The compound of formula (10) (0.6 g, 1.7 mmol) and n-butyllithium (0.16 g, 2.5 mmol) were taken and dissolved in tetrahydrofuran (100 mL) and stirred at room temperature for 30 minutes to form a dipolar body product; in addition, a reaction flask was additionally prepared, the compound 5 (0.59 g, 1.7 mmol) was taken and dissolved in tetrahydrofuran (50 mL), and stirred at a temperature of 0° C., and the dipolar body product was poured into the reaction flask and continuously stirred for 30 minutes, the reaction was terminated with ammonium chloride, the product was extracted with benzene, and concentrated and dried after water was removed with magnesium sulfate. The product was purified by HPLC to obtain 2-(10'Z, 13'E, 15'E)-10', 13', 15'-heptadecatrienyl-1,4-p-diacetyl benzene (341 Mg) (a compound of formula (11)), with a yield of 32%.

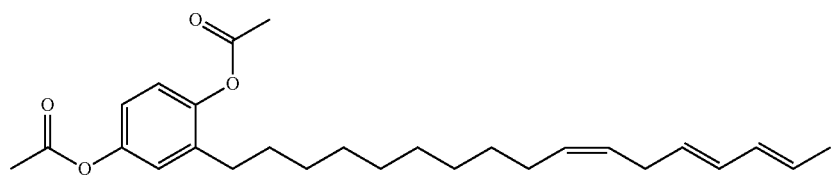
(11)

¹H NMR (500 MHz, CDCl₃) δ=1.26-1.33 (m, 12H, 3' to 8'-(CH₂)₆), 1.51-1.57 (m, 2H, 2'-CH₂), 1.71-1.78 (d, 3H, 17'-CH₃), 1.97-2.08 (m, 2H, 9'-CH₂), 2.28 (s, 3H, Acetyl-CH₃), 2.31 (s, 3H, Acetyl-CH₃), 2.48 (t, 2H, 1'-CH₂), 2.79 (t, 2H, 12'-CH₂), 5.26-5.45 (m, 2H, 10'-CH= and 11'-=CH), 5.49-5.62 (m, 2H, 13'-CH= and 16'-=CH), 5.93-6.05 (m, 2H, 14' to 15'-=CH—CH=), 6.91-6.94 (dd, 1H, 5-ArH), 6.96 (d, 1H, 3-ArH), 7.01 (d, 1H, 6-ArH).

Embodiment 1.12 Preparation of Compound of Formula (12)

The compound of formula (11) (22.5 g, 52.7 mmol) was reacted with sodium methoxide (0.6 g, 10.5 mmol) in methanol (300 mL), and stirred at room temperature for 20 hours, then the solution was neutralized with acid resin, the solution was extracted with benzene after being filtered, and finally organic solutions were combined and evaporated to dryness under reduced pressure. The product was purified by high performance liquid chromatography to obtain a solid product 2-(10'Z, 13'E, 15'E)-10', 13', 15'-heptadecatrienyl-1,4-p-diphenol (7.2 g) (a compound of formula (12)), with a yield of 39%.

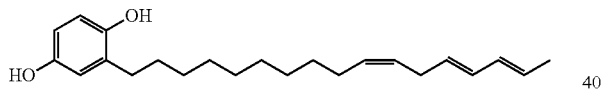

(12)

¹H NMR (500 MHz, CDCl₃) δ=1.27-1.34 (m, 12H, 3' to 8'-(CH₂)₆), 1.54-1.61 (m, 2H, 2'-CH₂), 1.78-1.71 (d, 3H, 17'-CH₃), 1.96-2.08 (m, 2H, 9'-CH₂), 2.53 (t, 2H, 1'-CH₂), 2.79 (t, 2H, 12'-CH₂), 4.31-4.33 (s, 2H, 1 and 4-ArOH), 5.33-5.45 (m, 2H, 10'-CH= and 11'-=CH), 5.49-5.62 (m, 2H, 13'-CH= and 16'-=CH), 5.95-6.05 (m, 2H, 14' to 15'-=CH—CH=), 6.55 (dd, 1H, 5-ArH), 6.61 (d, 1H, 3-ArH), 6.64 (d, 1H, 6-ArH); ¹³C NMR (500 MHz, CDCl₃) δ=18.15 (C-17'), 27.27 (C-9'), 29.4 (C-2'), 29.58-29.82 (C-3' to 8'), 30.19 (C-1'), 30.45 (C-12'), 113.15 (ArC-5), 116.1 (ArC-6), 116.93 (ArC-3), 127.08 (C-11'), 127.34 (C-16'), 130.1 (C-13'), 130.19 (ArC-2), 130.59 (C-14'), 131.1 (C-10'), 131.68 (C-15'), 147.49 (ArC-1), 149.48 (ArC-4).

Embodiment 2 Preparation of Compound of Formula (12')

LiAlH₄ (1.6 g, 42.9 mmol) and tert-butanol (12.3 mL, 128.7 mmol) were taken and reacted in a tetrahydrofuran solvent at a low temperature (−50° C.) for 30 minutes, and the compound (11) (2 g, 4.68 mmol) was additionally taken and dissolved in tetrahydrofuran, and added to a solution of LiAlH₄, and continuously stirred for 1 hour at a low temperature. Then the reaction was terminated by adding methanol, saturated ammonium chloride (30 mL) was added, and then extracted with ethyl acetate, organic layers were combined and evaporated to dryness under reduced pressure, and the product was purified by a silica gel column to obtain an impure compound 12' (1.1 g), with a yield of 72%. The impure reactant was extremely difficult to separate and purify. It can be found from NMR and MASS that the deacetylation reaction was not complete, and the product obtained by the reaction is in the shape of oil.

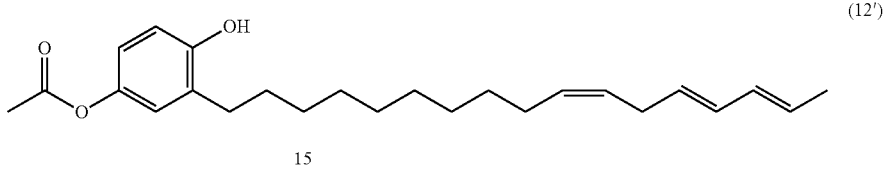

(12')

It can be confirmed from the above embodiments that the synthesis method provided in this application has its advantages, and the method uses a stable methylation-protected hydroquinone (1,4-dimethoxybenzene) as a starting material, which is more stable in chemical synthesis, and is highly efficient in the final deacetylation step, and the method can be applied to the preparation of hydroquinone with a long-chain olefin substituent to obtain a pure solid compound.

Although this application has been disclosed above by way of embodiments, it is not intended to limit this application. Various changes and modifications can be made by those of ordinary skill in the art without departing from the spirit and scope of this application. Therefore, the scope of protection of this application is defined by the appended claims.

[Symbol description] None

What is claimed is:
1. A method of preparing a hydroquinone derivative with heptadecatrienyl side chain, comprising:
(a) activating 1,4-dimethoxybenzene with n-butyl lithium in tetrahydrofuran, and then reacting with 1,10-dibromodecane at room temperature to obtain a compound of formula (1)

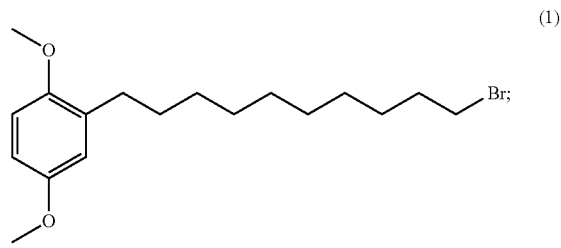 [SMILES: COc1ccc(OC)c(CCCCCCCCCCBr)c1]

(1)

(b) reacting the compound of formula (1) with boron tribromide to obtain a compound of formula (2)

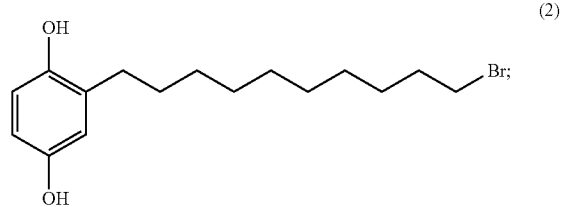 [SMILES: Oc1ccc(O)c(CCCCCCCCCCBr)c1]

(2)

(c) reacting the compound of formula (2) with acetic anhydride in pyridine to obtain a compound of formula (3)

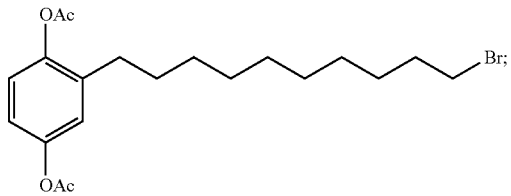
(3)

(d) reacting the compound of formula (3) with sodium iodide to obtain a compound of formula (4)

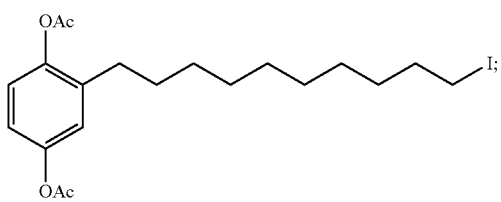
(4)

(e) treating the compound of formula (4) with sodium bicarbonate in dimethyl sulfoxide and benzene, and extracting with 0.1N HCl and saturated sodium chloride to obtain a compound of formula (5)

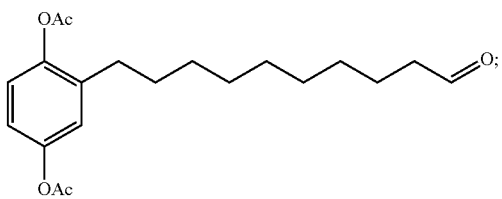
(5)

(f) subjecting the compound of formula (5) and heptadien-1-triphenylphosphonium iodide to a Wittig reaction and then a deacetylation reaction to obtain a hydroquinone derivative with heptadecatrienyl side chain, which is a compound of formula (11)

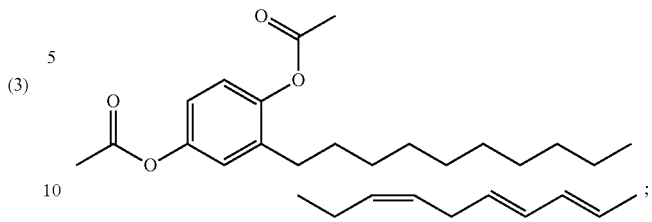
(11)

(g) reacting the compound of formula (11) with sodium methoxide in methanol at room temperature to obtain a compound of formula (12)

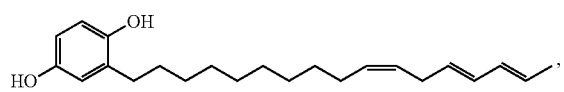
(12)

wherein the compound of formula (11) is reacted with the sodium methoxide in methanol at least 20 hours, then extracted with benzene, and organic layers are combined and evaporated to dryness under reduced pressure, then purified by a silica gel column to obtain the compound of formula (12).

2. The method according to claim 1, wherein the step (a) is carried out by activating 1,4-dimethoxybenzene with n-butyl lithium in tetrahydrofuran at −78° C. for 1 h and stirring at room temperature for 1 h, and then reacting with 1,10-dibromodecane at room temperature to obtain the compound of formula (1), then the compound of formula (1) is reacted with boron tribromide to demethylate to the compound of formula (2), and finally, the compound of formula (2) is reacted with acetic anhydride in pyridine at 110° C., 5 h to obtain the compound of formula (3).

3. The method according to claim 1, wherein the step (e) is carried out by the compound of formula (4) treated with sodium bicarbonate in dimethyl sulfoxide and benzene at 90° C. reflux for 4 h, and extracted with 0.1N HCl and saturated sodium chloride, after water removal with saturated sodium sulfate, obtaining the compound of formula (5).

* * * * *